United States Patent
Zhu et al.

(10) Patent No.: US 11,185,432 B2
(45) Date of Patent: Nov. 30, 2021

(54) DEVICES FOR TREATMENT OF CARPAL TUNNEL SYNDROME

(71) Applicants: Mengjia Zhu, Tempe, AZ (US); Wade Adams, Gilbert, AZ (US); Panagiotis Polygerinos, Gilbert, AZ (US)

(72) Inventors: Mengjia Zhu, Tempe, AZ (US); Wade Adams, Gilbert, AZ (US); Panagiotis Polygerinos, Gilbert, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 889 days.

(21) Appl. No.: 15/949,845

(22) Filed: Apr. 10, 2018

(65) Prior Publication Data

US 2018/0289522 A1 Oct. 11, 2018

Related U.S. Application Data

(60) Provisional application No. 62/484,002, filed on Apr. 11, 2017.

(51) Int. Cl.
*A61F 5/01* (2006.01)
*A61F 13/10* (2006.01)

(52) U.S. Cl.
CPC .............. *A61F 5/012* (2013.01); *A61F 5/013* (2013.01); *A61F 5/0118* (2013.01); *A61F 13/107* (2013.01); *A61F 2005/0155* (2013.01); *A61F 2005/0172* (2013.01); *A61F 2005/0188* (2013.01)

(58) Field of Classification Search
CPC ........ A61F 5/0118; A61F 5/012; A61F 5/013; A61F 13/107; A61F 13/108; A61F 2005/0155; A61F 2005/0172; A61F 2005/0188; A61F 5/01; A61F 5/0102; A41D 19/015
USPC ....... 602/13, 21, 64; 2/16, 20, 159, 162, 170
See application file for complete search history.

(56) References Cited

U.S. PATENT DOCUMENTS

| | | | | |
|---|---|---|---|---|
| 5,950,628 | A * | 9/1999 | Dunfee | A61F 5/024 128/874 |
| 2006/0118679 | A1* | 6/2006 | Delgado | G06F 3/039 248/118 |
| 2019/0015233 | A1* | 1/2019 | Galloway | B25J 9/0006 |
| 2019/0029914 | A1 | 1/2019 | Polygerinos et al. | |
| 2019/0167504 | A1 | 6/2019 | Polygerinos et al. | |

OTHER PUBLICATIONS

LeBlanc, K. E., and Cestia, W., 2011, "Carpal Tunnel Syndrome," Am. Acad. Fam. Physicians, 83(8), pp. 952-958.
Fagarasanu, M., and Kumar, S., 2003, "Carpal tunnel syndrome due to keyboarding and mouse tasks: A review," Int. J. Ind. Ergon., 31(2), pp. 119-136.

(Continued)

*Primary Examiner* — Keri J Nelson
(74) *Attorney, Agent, or Firm* — Snell & Wilmer L.L.P.

(57) ABSTRACT

The present disclosure describes soft-robotic wearable devices to treat and/or relieve Carpal Tunnel Syndrome, for example during typing assist applications. Soft actuators within the device adjust the angle of the wearer's wrist angle dynamically to achieve a neutral angle, alleviating the pressure on the median nerve and relieving Carpal Tunnel Syndrome strain.

11 Claims, 7 Drawing Sheets

(56) References Cited

OTHER PUBLICATIONS

Rempel, D., Barr, A., Brafman, D., and Young, E., 2007, "The effect of six keyboard designs on wrist and forearm postures," Appl. Ergon., 38(3), pp. 293-298.
Rempel, D. M., Keir, P. J., and Bach, J. M., 2009, "NIH Public Access," Sci. York, 26(9), pp. 1269-1273.
U.S. Appl. No. 16/396,409.
U.S. Appl. No. 16/276,064.
U.S. Appl. No. 16/381,637.

* cited by examiner

DEVICES FOR TREATMENT OF CARPAL TUNNEL SYNDROME

CROSS-REFERENCE TO RELATED APPLICATIONS

This application claims priority to, and the benefit of, U.S. Provisional Patent Application No. 62/484,002 filed on Apr. 11, 2017 and entitled "DEVICES FOR TREATMENT OF CARPAL TUNNEL SYNDROME", the entire contents of which are incorporated by reference herein for all purposes.

TECHNICAL FIELD

The present disclosure relates to devices for adjusting wrist position, and in particular, to wearable devices for relief from Carpal Tunnel Syndrome.

BACKGROUND

Carpal Tunnel Syndrome ("CTS") is caused by long-term stress applied to the median nerve, such as during typing and other types of repetitive wrist motions and positioning. Wrists can become inflamed and swollen due to pressure from the palmar carpal ligament causing numbness, stiffness, and in some cases, severe pain. Treatments for CTS include devices which restrict motion of the wrist.

Traditional devices for treatment of CTS statically immobilize or partially immobilize the wrist. These devices can be uncomfortable when worn for extended periods of time. Further, rigid and/or immobilization of the wrist does not account for dynamic movement of the wrist, and can interfere with activities such as typing. Therefore, a device which provides dynamic treatment of CTS remain desirable.

SUMMARY

In an embodiment of the present disclosure, a wearable wrist device can comprise a wearable sleeve conformable to the wrist, a first soft actuator comprising at least one pleat positioned along a top surface of the wearable sleeve, a second soft actuator positioned along a bottom surface of the wearable sleeve, an air valve in fluid communication with the first soft actuator and the second soft actuator, and a control system comprising an inertial measurement unit in electrical communication with a microcontroller. The control system can further comprise at least one pressure sensor in communication with the microcontroller. The first soft actuator can comprise multiple pleats. The second soft actuator can also comprise multiple pleats. The second soft actuator can comprise the same, fewer, or more pleats than the first soft actuator. At least one strap can be coupled to the wearable sleeve. The wearable sleeve can comprise a breathable fabric. An air source can be coupled to the air valve.

The contents of this summary section are intended as a simplified introduction to the disclosure, and are not intended to be used to limit the scope of any claim.

BRIEF DESCRIPTION OF THE DRAWINGS

With reference to the following description and accompanying drawings.

DETAILED DESCRIPTION

The following description is of various exemplary embodiments only, and is not intended to limit the scope, applicability, or configuration of the present disclosure in any way. Rather, the following description is intended to provide a convenient illustration for implementing various embodiments including the best mode. As will become apparent, various changes may be made in the function and arrangement of the elements described in these embodiments without departing from principles of the present disclosure.

The present disclosure describes wearable devices which provide dynamic treatment of CTS and/or CTS symptoms. While not wishing to be bound by a particular theory of operation, it is believed that maintaining the wrist in a neutral plane during repetitive activities, such as typing, may reduce CTS symptoms. In various embodiments, a wearable device is configured to maintain a neutral wrist angle during wrist movement by utilizing a control system to pressurize soft actuators within a sleeve surrounding the wrist of a user.

Wearable devices of the present disclosure may be comfortable for a user to wear for an extended period of time, and made from materials that allow the skin to breath. The device can detect the changes of the wrist-plane angle in real-time and actively adjust the soft actuators to move the wrist plane and return it to a neutral state. Additionally, dynamically-adjustable cushioning support is provided on the proximal side of the palm that can conform around objects and surfaces to provide comfort and height adjustment as well as to not interfere with typing. Safety requirements such as the ability to release pressure quickly are also included in the device.

Figure 1:
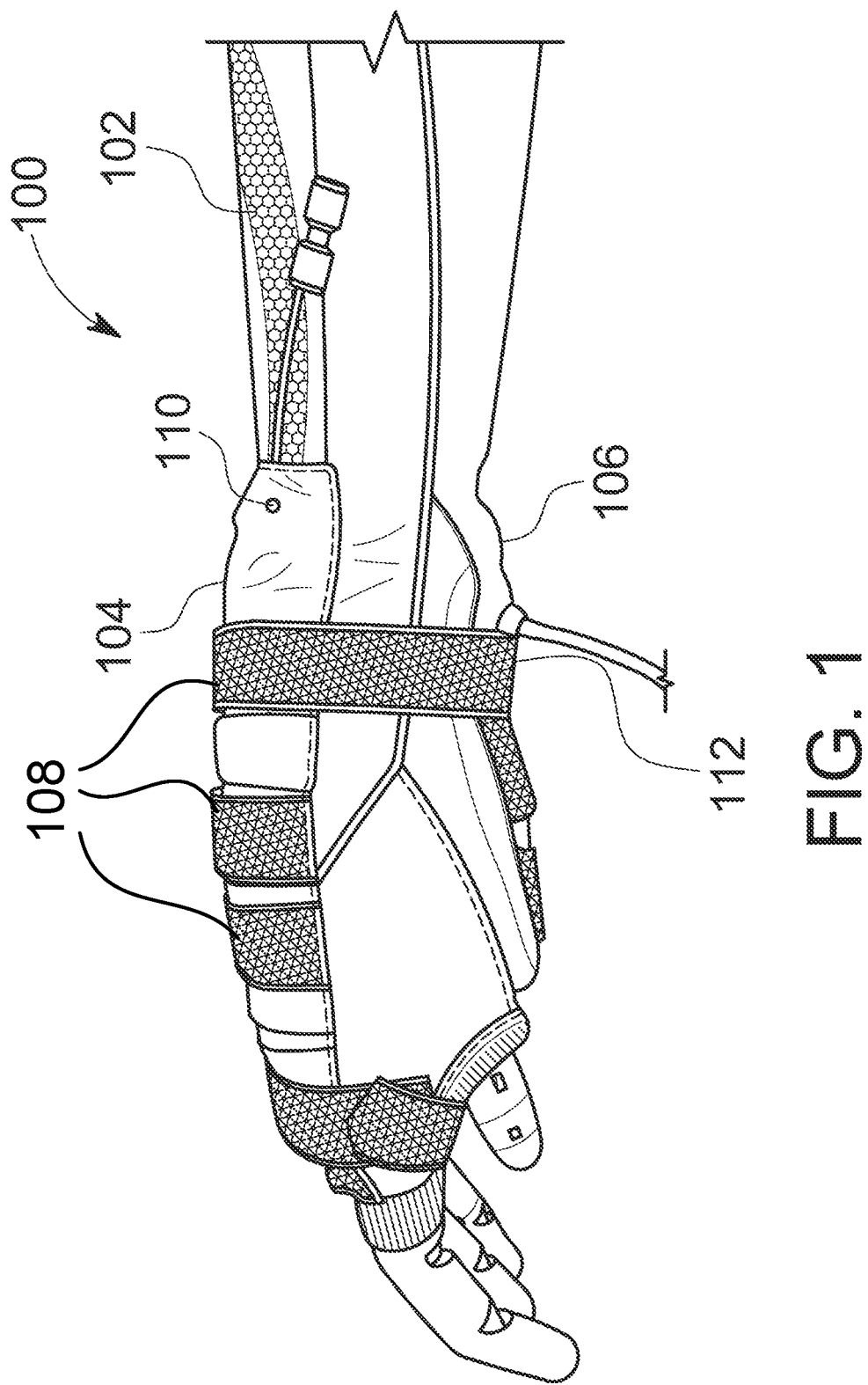
FIG. 1 illustrates a side view of a wearable wrist support device in accordance with various embodiments.

With reference to FIG. 1, a wearable CTS treatment device 100 is illustrated. In various embodiments, device 100 comprises a wearable wrist brace that can be easily donned and removed. Device 100 can comprise a dual soft actuator system. For example, one soft actuator can be positioned at the bottom of the sleeve to help lift the wrist and another soft actuator can be positioned at the top to flex the wrist. Adjustment of the angle of a wearer's wrist can be achieved by dynamically pressurizing the soft actuators, which can comfortably assist the wrist to return to a neutral angle.

Device 100 may, for example, be able determine the position of the wrist (relative to the neutral angle) utilizing information provided from one or more sensors within device 100. Device 100 can further comprise a control system capable of reacting to the position of the wrist and adjusting the position by actuating one or more soft actuators.

In various embodiments, device 100 comprises a sleeve 102. Sleeve 102 can comprise, for example, a fabric material, such as an elastic fabric. In various embodiments, sleeve 102 comprises a breathable fabric, which may be more comfortable than a non-breathable fabric when worn for extended periods of time.

Device 100 further comprises a first soft actuator 110. For example, first soft actuator 110 can be a top actuator positioned at or near a top surface 104 of sleeve 102. In various embodiments, first soft actuator 110 comprises an air bladder. In such embodiments, air can be injected in to first soft actuator 110 to cause the air bladder to change shape.

With reference to FIGS. 2A-2D, a first soft actuator 110 is illustrated in various views. In various embodiments, first soft actuator 110 comprises a thermoplastic material. First soft actuator 110 can be fixedly coupled to sleeve 102 by, for example, sewing or gluing, or removably coupled to sleeve 102. For example, sleeve 102 can comprise a pocket or opening into which first soft actuator 110 is inserted and/or positioned. Any manner of coupling first soft actuator 110 and sleeve 102 is within the scope of the present disclosure.

Figure 2A:
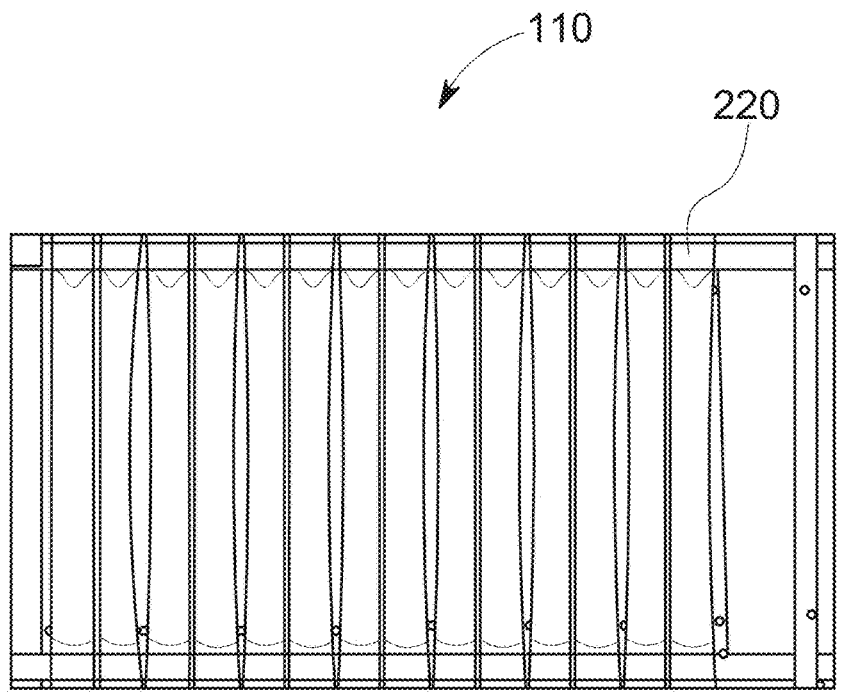
FIG. 2A illustrates a top view of a pleated air bladder of a wearable wrist support in accordance with various embodiments.
Figure 2B:
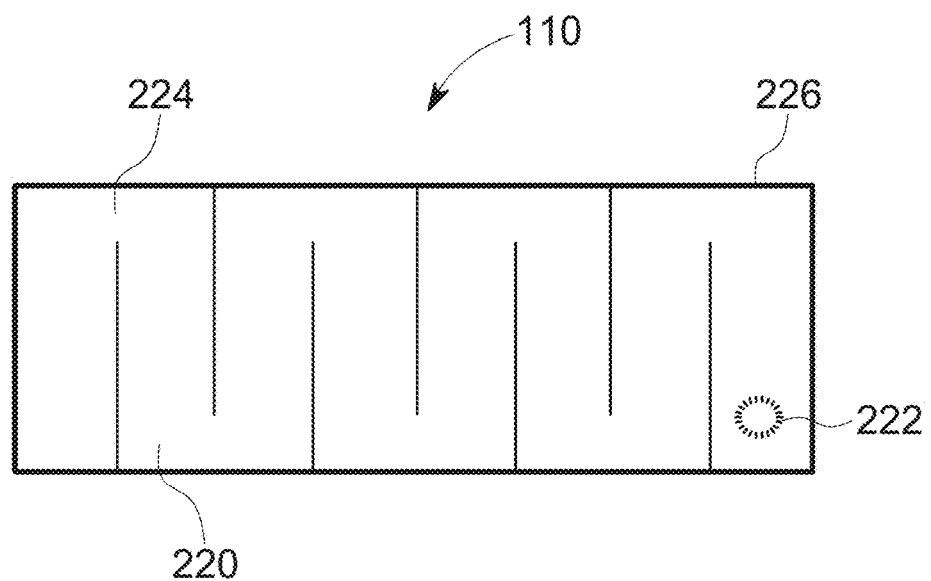
FIG. 2B illustrates a schematic representation of pleated air bladder of FIG. 2A in accordance with various embodiments.

In various embodiments, first soft actuator 110 comprises multiple pleats 220. As illustrated in FIG. 2B, multiple pleats 220 can be in fluid communication with one another via multiple channels 224 positioned between pleats 220. First soft actuator 110 can further comprise one or more non-pleated segments 226. In various embodiments, first soft actuator 110 further comprises an air inlet valve 222 through which air can be injected into first soft actuator 110.

With reference back to FIG. 1, device 100 can further comprise a second soft actuator 112. For example, second soft actuator 112 can be a bottom actuator positioned at or near a bottom surface 106 of sleeve 102. Similar to first soft actuator 110, in various embodiments, second soft actuator 112 comprises an air bladder having zero, one, or multiple pleats. In such embodiments, air can be injected into second soft actuator 112 to cause the air bladder to change shape.

In various embodiments, the simultaneous use of first soft actuator 110 and second soft actuator 112 allows device 100 to utilize relatively low pressures to make corrective actions to the wrist, which can decrease power requirements and the likelihood of a failure in the device. Further, first soft actuator 110 and second soft actuator 112 can comprise air bladders having a different number of pleats from one another. For example, first soft actuator 110 can comprise more pleats than second soft actuator 112. Although described with reference to specific physical embodiments, any combination of pleats of first soft actuator 110 and second soft actuator 112 is with the scope of the present disclosure.

Device 100 can further comprise, for example, an air source (not illustrated). In various embodiments, the air source is an external air pump coupled to first soft actuator 110 and/or second soft actuator 112. In other embodiments, the air source (such as a small pump or compressor) is coupled to sleeve 102, and external power is supplied to the air source. Moreover, a battery coupled to the device may power the air source. Any manner of providing pressurized air to device 100, first soft actuator 110, and second soft actuator 112 is within the scope of the present disclosure.

In various embodiments, device 100 further comprises a control system (not illustrated). For example, a control system can be positioned within device 100, and may comprise a microcontroller in electrical communication with one or more sensors to determine the position of the wrist of a wearer. In various embodiments, the control system comprises one or more pressure sensors, which record the internal pressures of first soft actuator 110 and/or second soft actuator 112. Further, the control system can comprise an inertial measurement unit (IMU) to detect the position of the wrist of the wearer. In such embodiments, the IMU may be able to sense improper positioning of the wrist relative to the neutral angle. In various embodiments, the IMU can be fixed on the upper part of the wrist, under first soft actuator 110.

With further reference to FIG. 1, device 100 can further comprise one or more straps 108 coupled to sleeve 102. For example, straps 108 can comprise hook and loop straps attached to sleeve 102 and configured to comfortably secure sleeve 102 to the hand of the wearer, while allowing for adequate torque generation about the wrist and soft force distribution when the first soft actuator 110 and/or second soft actuator 112 are pressurized. Straps 108 can be secured (such as via sewing) to sleeve 102 at positions around the first soft actuator 110 and/or second soft actuator 112 to ensure that the soft actuators do not swell radially when pressurized. Correction of the wrist angle may, for example, be achieved by dynamically pressurizing the first soft actuator 110 and/or second soft actuator 112 to comfortably assist the wrist in the return to a neutral angle.

Experiment

Figure 3A:
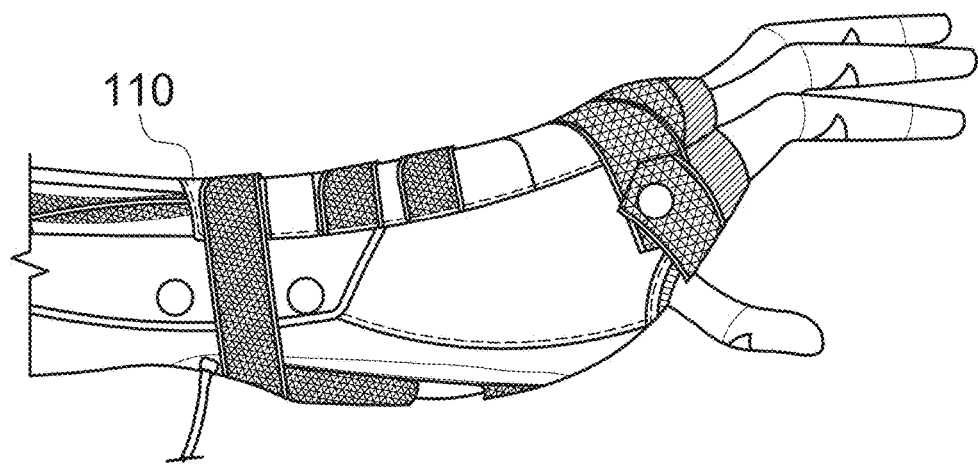
FIG. 3A illustrates a side view of the initial position of the wearable wrist support device of Experiment 1.
Figure 3B:
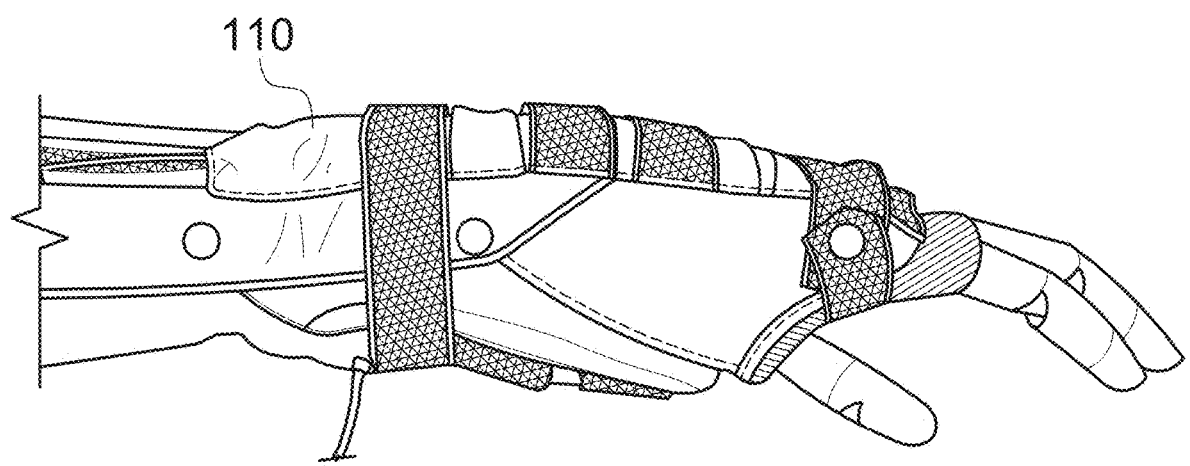
FIG. 3B illustrates a side view of the final position of the wearable wrist support device of Experiment 1.

With initial reference to FIGS. 3A and 3B, a motion experiment was conducted on a passive hand model to demonstrate the functionalities of a wearable wrist device having a pleated air bladder, in accordance with the present disclosure.

A tri-camera motion caption tool (OptiTrack V120: TRIO) was used to capture the location of three infrared markers in 3D space. The three markers were fixed to the side of the passive hand model: one behind the wrist, one at the wrist joint, and one near the joint of the index and the palm. All of the markers were placed in a straight line along the length of the model when the wrist angle was zero. FIG. 3A illustrates the initial position of the wearable wrist device. In Experiment 1, a 200-gram weight was used to lift the passive hand up to a certain angle which needs to be adjusted to neutral position by the pleated air bladder of the wearable wrist device, illustrated in FIG. 3B as the final position of the wearable wrist device. Three measurements were taken during the test in addition to motion tracking; the pressures for both airbags and the IMU roll reading which provides a relative angle derived from the on-board accelerometer. The angle was also calculated using the position of the markers from motion tracking to compare with the IMU reading.

Figure 4A:
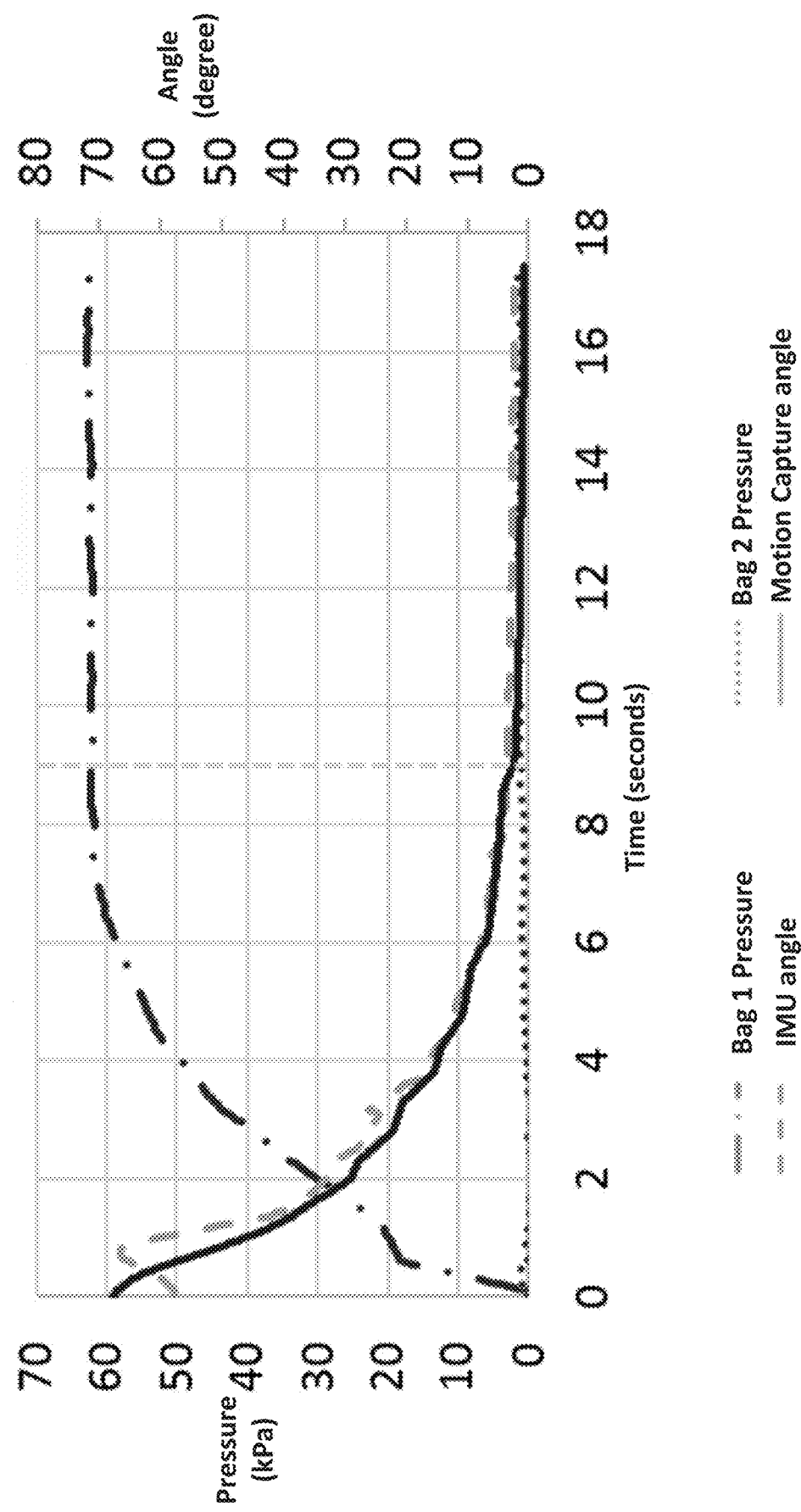
FIG. 4A illustrates the results of Experiment 1, including a graphical reproduction of the pressure within a first air bladder compared to time of inflation and angle of a wrist in accordance with an embodiment.

With initial reference to FIG. 4A, the results of Experiment 1 are illustrated. The data was recorded when the pleated air bladder of the wearable wrist device began inflating. As the pressure increased in the pleated air bladder, the angle of the wrist plane decreased.

When the pleated air bladder of the device of Experiment 1 inflated, its pleated structure allowed it to bend and apply a rotational moment to the wrist, which reduced the angle to a neutral position. Typing in a neutral wrist angle can help reduce the applied strain to the palmar carpal ligament as well as the inflammation and swelling of the median nerve.

Experiment 2

The same tri-camera motion caption tool (OptiTrack V120: TRIO) as was used in Experiment 1 was used to capture the location of three infrared markers in 3D space. As in Experiment 1, the three markers were fixed to the side of the passive hand model: one behind the wrist, one at the wrist joint, and one near the joint of the index and the palm. All of the markers were placed in a straight line along the length of the model when the wrist angle was zero. The passive hand model was fitted with a wearable device having a non-pleated air bladder.

The second experiment demonstrated that the non-pleated air bag acted as a cushion to help lift the wrist up by a height similar to the one of a keyboard. The hand model was relaxed on the ground plane and only the non-pleated air bag was inflated. Pressure and the motion tracking data were collected and the displacement (height) from the ground plane of the wrist marker was analyzed. All the measurements were time synchronized and the analyzed data can be used to determine the function of the airbags.

Figure 3C:
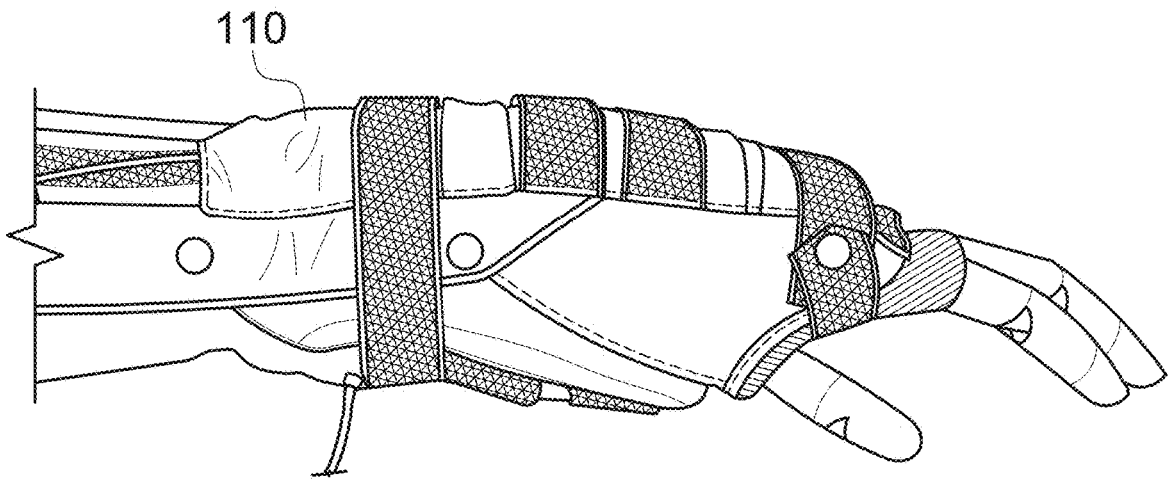
FIG. 3C illustrates a side view of the initial position of the wearable wrist support device of Experiment 2.
Figure 3D:
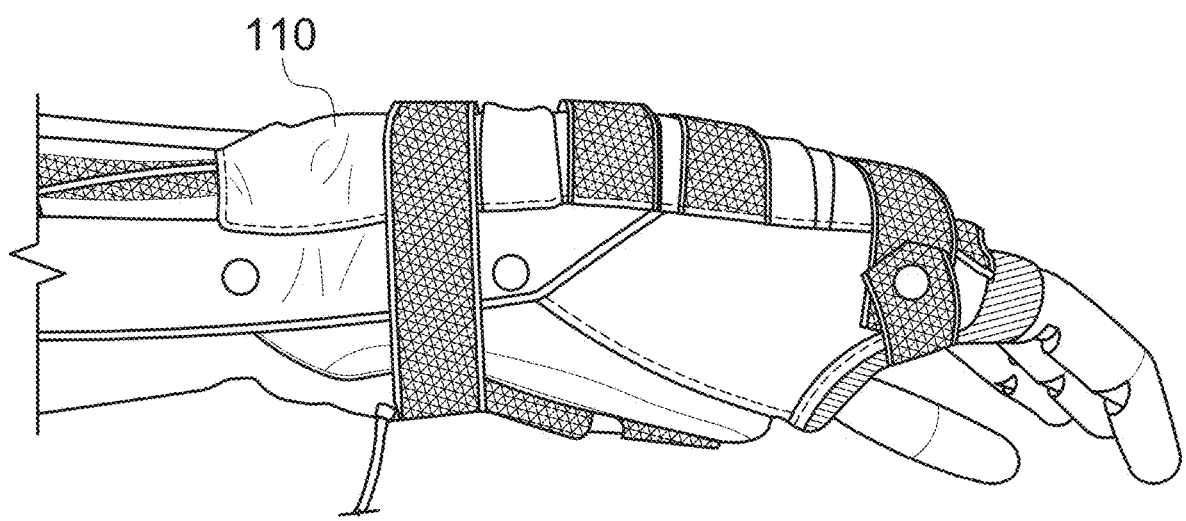
FIG. 3D illustrates a side view of the final position of the wearable wrist support device of Experiment 2.

With initial reference to FIGS. 3C and 3D, when the non-pleated air bag was pressurized, the initial position (illustrated in FIG. 3C) transitioned to the final position (illustrated in FIG. 3D), in which the distance between the table and the hand increased.

Figure 4B:
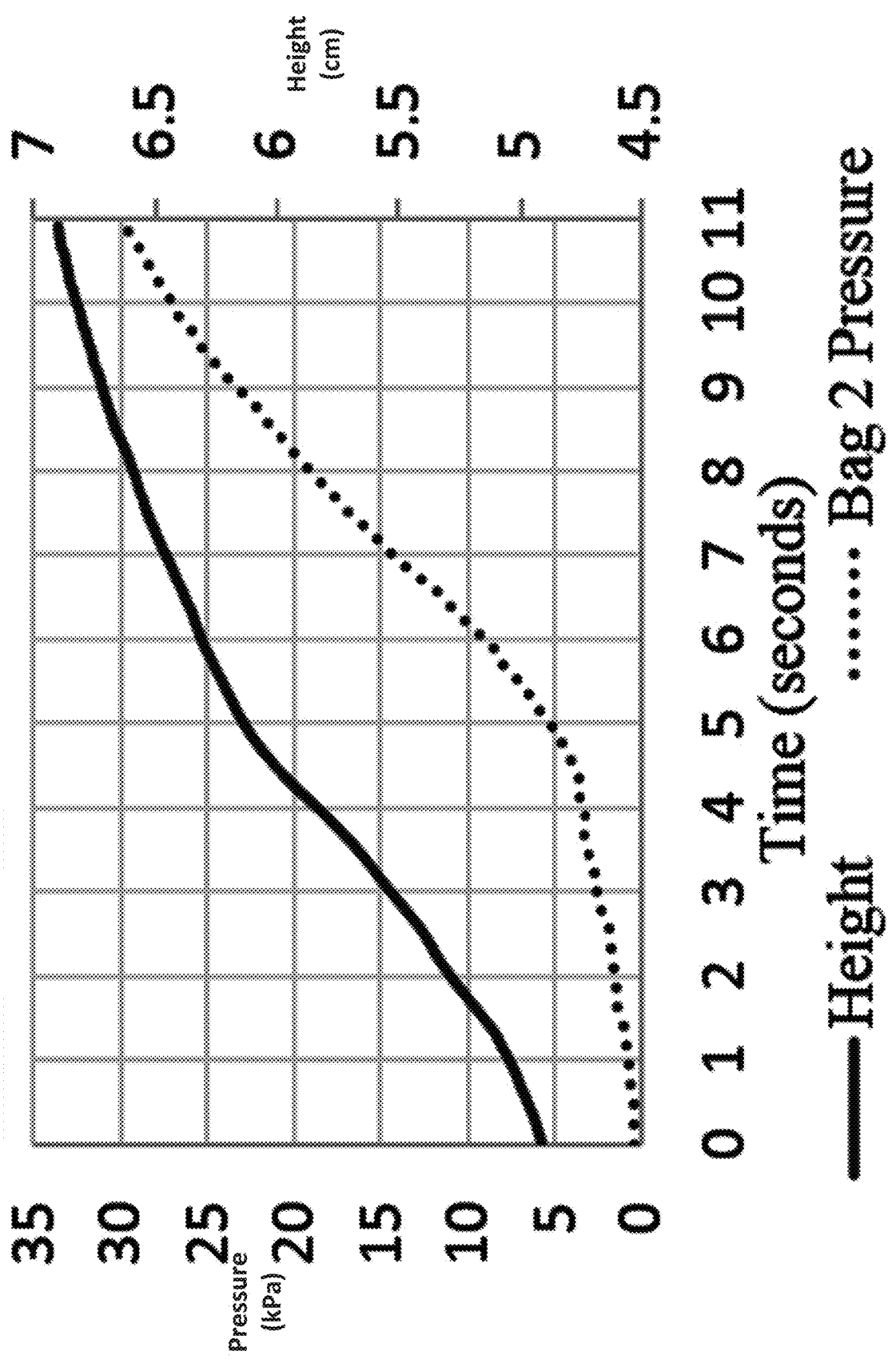
FIG. 4B illustrates the results of Experiment 2, a graphical reproduction of the pressure within a second air bladder compared to time of inflation and height of a wrist in accordance with an embodiment.

FIG. 4B illustrates the results of Experiment 2. During Experiment 2, both the pressure of the non-pleated air bag and the vertical height of the wrist increased. The wearable wrist device of Experiment 2 was able to lift a wrist from a height of 4.8 cm to a height of 6.8 cm measured from the top of the ground plane. The increment 2.0 cm is slightly higher than a measured keyboard height (1.9 cm). This lift was produced by a total pressure of 31 kPa. The angle of the wrist plane is not included in this experiment as the non-pleated air bag device is responsible for increasing the distance from the table to the wrist and providing a cushion for the user (not changing the angle of the wrist plane). By inflating the non-pleated air bag, the wrist sits on a cushioned surface which is at the same height level of the keyboard to provide more comfort for the user.

Figure 2C:
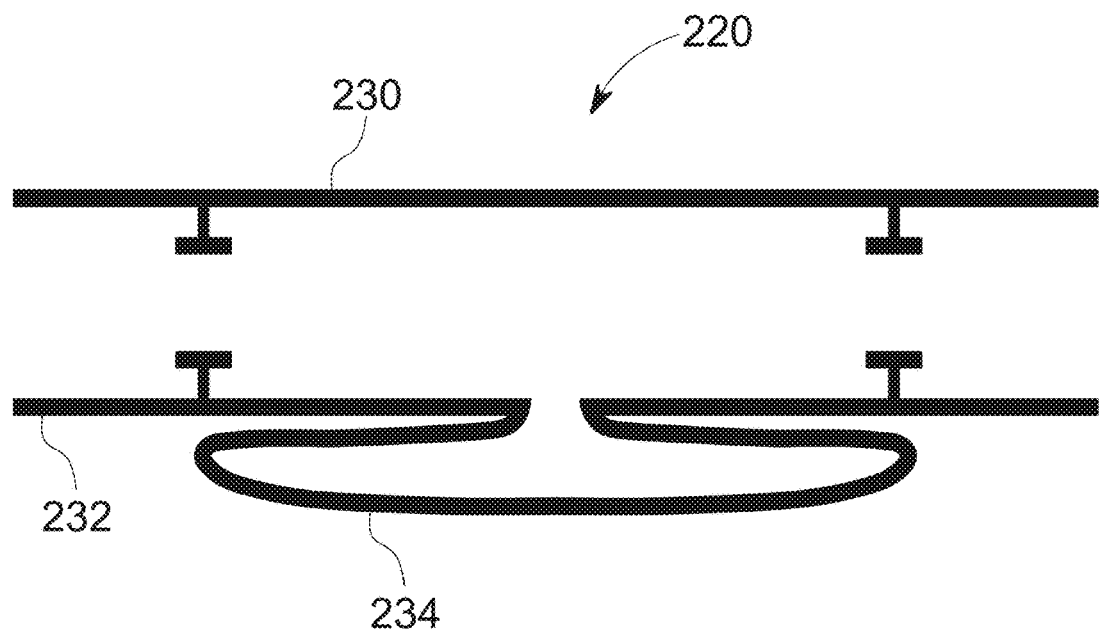
FIG. 2C illustrates a schematic representation of a pleat of the pleated air bladder of FIG. 2A.
Figure 2D:
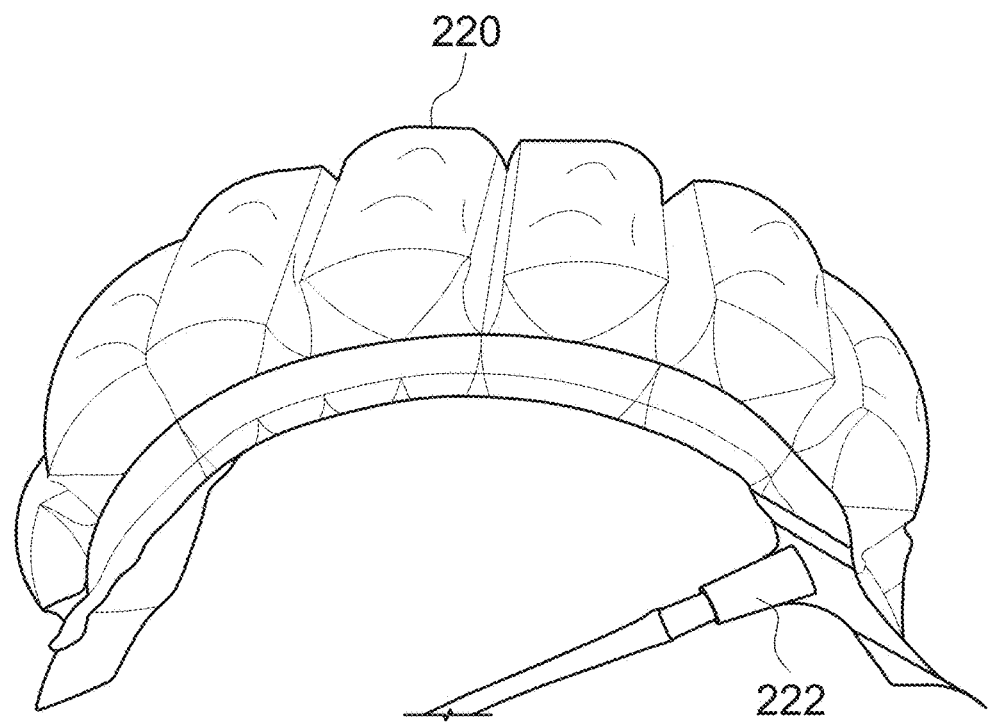
FIG. 2D illustrates a pressurized pleated air bladder in accordance with various embodiments.

In an exemplary embodiment, first soft actuator 110 (upper air bag) comprises an eight-flanged thermoplastic polyurethane (TPU) air bladder inside of a fabric cover. The air bladder is 6-thick when not pressurized. With reference to FIGS. 2B and 2C, the eight flange units are seven pleats 220 designed to achieve the wrist flexion requirement by having a different upper length 230 and lower length 232. The ratio of upper length 230 to lower length 232 for each pleat 220 is 3.0:1.0. The difference between upper length 230 and lower length 232 is illustrated as additional length 234. The length and width of each pleat is 6.350 cm (2.5 in) and 1.905 cm (0.75 in). The eighth flange unit has the same upper length and lower length of 1.905 cm. An impulse heat sealing machine with 2 and 5 mm wide effective sealing widths may be used to seal the inner sides between flange units and the outer sides of the air bladder. When first soft actuator 110 is pressurized, the air bladder bends longitudinally and contracts transversely, as shown in FIG. 2D. The fabric cover is designed to have a similar structure that allows the bladder to bend freely longitudinally, but restricting radial expansion when it is pressurized.

Second soft actuator 112 (lower air bag) is designed to lift the wrist up by a height similar to that of a keyboard. Second soft actuator 112 comprises a three-unit TPU bladder and a fabric outer cover. The size of each unit is 6.350 cm (2.5 in) by 5.080 cm (2 in). All three units have the same upper and lower length, as the second soft actuator is not configured to bend (in contrast to first soft actuator 110).

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection.

What is claimed is:

1. A device for treatment of nerve compression of a wrist, the device comprising:
    a wearable sleeve conformable to the wrist;
    a first soft actuator comprising a plurality of pleats positioned along a top surface of the wearable sleeve;
    a second soft actuator positioned along a bottom surface of the wearable sleeve;
    a first strap sewed to the wearable sleeve around the first soft actuator to ensure the first soft actuator does not swell radially when pressurized;
    a second strap sewed to the wearable sleeve around the second soft actuator to ensure the second soft actuator does not swell radially when pressurized;
    an air valve in fluid communication with the first soft actuator and the second soft actuator; and
    a control system comprising an inertial measurement unit in electrical communication with a microcontroller, wherein the inertial measurement unit is fixed under the first soft actuator, and
    wherein the second soft actuator is positioned so as to raise the wrist in response to the second soft actuator being pressurized.

2. The device of claim 1, wherein the second soft actuator comprises multiple pleats.

3. The device of claim 2, wherein the second soft actuator comprises fewer pleats than the first soft actuator.

4. The device of claim 1, wherein the wearable sleeve comprises a breathable fabric.

5. The device of claim 1, further comprising an air source coupled to the air valve.

6. The device of claim 5, wherein the first soft actuator is pressurizable via the air source.

7. The device of claim 6, wherein the second soft actuator is pressurizable via the air source.

8. The device of claim 1, wherein the control system further comprises at least one pressure sensor in communication with the microcontroller.

9. The device of claim 1, wherein the first soft actuator comprises an eight-flanged thermoplastic polyurethane air bladder disposed inside of a fabric cover.

10. The device of claim 9, wherein the first soft actuator, when pressurized, bends longitudinally and contracts transversely.

11. The device of claim 1, further comprising a battery coupled to the control system.

\* \* \* \* \*